(12) United States Patent
Ryckman et al.

(10) Patent No.: US 6,476,248 B1
(45) Date of Patent: Nov. 5, 2002

(54) HYDROXYTHIOL GRIGNARD REACTION SYNTHESIS

(75) Inventors: David Ryckman, San Diego, CA (US); Mingbao Zhang, Danville, NJ (US); Guohua Chen, Parsippany, NJ (US)

(73) Assignee: Honeywell International, Inc., Morristown, NJ (US)

( * ) Notice: Subject to any disclaimer, the term of this patent is extended or adjusted under 35 U.S.C. 154(b) by 0 days.

(21) Appl. No.: 09/515,544

(22) Filed: Feb. 29, 2000

Related U.S. Application Data

(62) Division of application No. 09/215,691, filed on Dec. 18, 1998, now Pat. No. 6,054,623.

(51) Int. Cl.$^7$ .................. C07C 321/28; C07C 323/29; C07F 7/08; C07F 7/10
(52) U.S. Cl. ............... 556/419; 556/486; 556/489; 564/162; 564/440; 568/40
(58) Field of Search ............... 556/489, 486, 556/419; 564/162, 440; 568/40

(56) References Cited

U.S. PATENT DOCUMENTS

| | | | | | |
|---|---|---|---|---|---|
| 1,968,906 | A | * | 8/1934 | Palmer ................ | 260/154 |
| 2,286,701 | A | * | 6/1942 | Werner ................ | 430/187 |
| 2,497,422 | A | * | 2/1950 | Snyder et al. ........ | 260/609 |
| 2,820,780 | A | * | 1/1958 | Gutcho ................ | 530/336 |
| 2,921,964 | A | * | 1/1960 | Ramsden .............. | 260/607 |
| 3,086,997 | A | * | 4/1963 | Warner ................ | 260/609 |
| 3,479,407 | A | * | 11/1969 | Laufer ................ | 260/608 |
| 3,883,598 | A | * | 5/1975 | Guthrie et al. ...... | 260/609 R |
| 3,981,809 | A | | 9/1976 | Caspari .............. | 252/327 E |
| 4,006,186 | A | * | 2/1977 | Engels et al. ........ | 260/577 |
| 4,281,202 | A | * | 7/1981 | Buchholz et al. ..... | 568/62 |
| 4,542,241 | A | * | 9/1985 | Gray et al. .......... | 568/62 |
| 4,734,527 | A | * | 3/1988 | Krauss ............... | 568/47 |
| 4,873,346 | A | * | 10/1989 | Anderson ............. | 548/157 |
| 4,948,827 | A | * | 8/1990 | Christidis ........... | 524/392 |
| 4,985,586 | A | * | 1/1991 | Arretz et al. ........ | 560/18 |
| 5,705,702 | A | * | 1/1998 | Osawa et al. ......... | 568/74 |
| 5,776,699 | A | * | 7/1998 | Klein et al. ......... | 435/7.2 |
| 5,834,393 | A | * | 11/1998 | Jacobsen et al. ...... | 502/152 |
| 5,834,506 | A | * | 11/1998 | Boyer et al. ......... | 514/460 |

FOREIGN PATENT DOCUMENTS

| WO | WO 96/18688 | 6/1996 |
|---|---|---|
| WO | 98 52929 A | 11/1998 |

OTHER PUBLICATIONS

Bugerenko et al. Chemical Abstracts 101:130781 (1984).*
Nakano et al. Chemical Abstracts 120:55194 (1994).*
Oriyama et al. Chemical Abstracts 125:168110 (1996).*
Bastian et al., Chemical Abstracts 127:176339 (1997).*
J Chem Soc by Watson and Dutt 121 pp 2414–2419, 1922.*
J Amer Chem Soc By Djerassi vol. 77, pp 568–571, 1955.*
Gazz Chim Ital 99 by Cabiddu pp 1095–1106, 1969.*
CA:119:117042 ab of Zh Org Khim by Ganushchak 28(3) pp 531–6, 1992.*
Watson et al., *J. Chem. Soc.*, 121, 2414 (1922).
Yiannios et al., *J. Org. Chem.*, 28, 3246 (1963).
Cohen et al., *J. Org. Chem.*, 42(12), (1977).
Allen et al., *Org. Synth. Coll.*, 1, 580 (1943).
Ungnade et al., *Org. Synth. Coll.*, 3, 130 (1995).
Foster, *Org. Synth. Coll.*, 3, 771 (1955).
Narch, *Advanced Organic Chemistry* (Fourth Ed., J. Wiley & Sons, New York, NY, 1992), 613–614.
Derwent Publications Ltd., London, GB; AN 1986–080848, xp002135611 & SU 1 177 296 a (Veksler KV), Sep. 7, 1985 abstract.
Z.Y. Wang et al. J. Org. Chem. vol. 57, No. 9, 1992, pp. 2751–2753, XP002135608, p. 2751, scheme I, p. 2752, col. 2, p. 2753, col. 1, preparation of 1h.
N Abdou et al; Pharmazie, vol. 33, No. 4, 1978, pp. 190–191, XP00089157 p. 191, experimental preparation of compound 3.2 idem.
Database Chemabs, STN, CAPLUS accession No. 1986:50661, XP002135610 abstract & JP 60 146866 a (Ricoh Co. Ltd.) Aug. 2, 1985.
A.V. Anisimov Et Al; Chem. Heterocycl. Comp. vol. 28, No. 9, 1992, pp. 1084–1086, XP 000864533, p. 1084, first scheme; p. 1086, lines 1–3.
Chemical Abstracts, vol. 104, No. 19, May 12, 1986 Columbus, Ohio, US, Abstract No. 168113d, XP002135609 abstract & JP 60 199871 a (Nippon Kayaku Co. Ltd.) Oct. 9, 1985.

(List continued on next page.)

Primary Examiner—Peter O'Sullivan
(74) Attorney, Agent, or Firm—Colleen D. Szuch

(57) ABSTRACT

A method for the preparation of hydroxythiol compounds by reacting a hydroxyl-protected halide compound having the structure:

X—R—OPg with magnesium in a Grignard-suitable solvent to form a hydroxyl-protected magnesium halide compound, wherein R is selected from substituted or unsubstituted aliphatic radicals, substituted or unsubstituted cyclic aliphatic radicals, substituted or unsubstituted aromatic radicals, substituted or unsubstituted araliphatic radicals and substituted or unsubstituted heterocyclic radicals; Pg is a protecting group; and X is selected from the group consisting of F, Cl, Br and I; then reacting said hydroxyl-protected magnesium halide compound with sulfur in the Grignard-suitable solvent to form a hydroxyl-protected thiomagnesium halide compound; and hydrolyzing the protected hydroxyl group to form a hydroxythiomagnesium halide compound and converting the thiomagnesium halide to a thiol; wherein the protecting group is selected so that species formed by the de-protection of the protecting group are inert toward thiols, or the method further includes the step of removing the protecting group species formed by de-protection of the hydroxyl group from the reaction mixture before converting the thiomagnesium halide to a thiol.

3 Claims, No Drawings

OTHER PUBLICATIONS

Y. Hitotsuyanagi Et Al. "Synthesis of 4-thia-2-azapodophyllotoxin, a new analogue of the antitumour lignan podophyllotoxin" Journal of the Chemical Society, Perkin Transactions 1, No. 11, Jun. 7, 1995, pp. 1387-1390, XP002139429 Royal Society of Chemistry, Letchworth, GB ISSN: 0300-922X p. 1389, left-hand column, paragraph 1.

J. Tercio, Et Al. "Radikalionen 89. Einelektronene-Oxidationen von Diaryldisulfiden mit A1C13/H2CC12" Phosphorus, Sulfur and Silicon and the Related Elements, vol. 68, No. 1-4, 1992, pp. 261-291, XP000913633 Gordon and Breach Science Publishers, Amsterdam, NL issn: 1042-6507 p. 289, paragraph 3.

H. Bock, Et Al. "Radikalionen 89. Einelektronene-Oxidationen von Diaryldisulfiden mit A1C13/h2CC12" Phosphorus, Sulfur and Silicon and the Related Elements, vol. 68, No. 1-4, 1992, pp. 261-291, XP000913633 Gordon and Breach Science Publishers, Amsterdam, NL ISSN: 1042-6507 p. 289, paragraph 3.

T. Zincke, Et Al.: "Uber 1-Phenol-3-mercaptan" Berichte Der Deutschen Chemischen Gesellschaft, vol. 47, 1914, pp. 923-933, XP002139431 Verlag Chemie, Weinheim, DE p. 925, last paragraph—p. 927.

G. E. Boswell, Et Al.: "Synthesis, stereochemistry, and opioid binding activity of heterocyclic analogues of BW373U86" Journal of Heterocyclic Chemistry, vol. 32, No. 6, Nov. 1995, pp. 1801-1818, XP002139432 Heterocorporation, Provo, US ISSN: 0022-152X compoun 19.

M.E. Jung, Et Al.: "Quantitative dealkylation of alkyl ethers via treatment with trimethylsilyl iodide. A new method for either hydrolysis" Journal of Organic Chemistry, Nov. 11, 1977, pp. 3761-3764, XP002139433 American Chemical Society, Washington, DC US ISSN: 0022-3263 compound 3t.

* cited by examiner

HYDROXYTHIOL GRIGNARD REACTION SYNTHESIS

This application is a divisional of application Ser. No. 09/215,691 filed Dec. 18, 1998 now U.S. Pat. No. 6,054,623. The entire disclosure of the prior application(s) is hereby incorporated by reference in its entirety.

FIELD OF THE INVENTION

The present invention relates to the preparation of hydroxythiol compounds, and, more specifically, to the preparation of isomerically pure hydroxythiophenols. In particular, the present invention relates to a commercially feasible hydroxythiophenol synthesis in which significant quantities of the isomerically pure reaction product are obtained.

DESCRIPTION OF THE PRIOR ART

General methods for the preparation of thiol compounds using the Grignard-sulfur reaction are known in the literature. Halide compounds are reacted with magnesium metal and then sulfur powder to produce a thiol. The extension of the Grignard reaction to hydroxy halide compounds requires protection of the reactive hydroxyl group. However, even when hydroxyl group protection is employed, low yields are obtained.

Isomerically pure hydroxythiophenols are important reagents and starting materials for a variety of pharmaceutical, agrochemical and chemical processes. 3-Hydroxythiophenol, in particular, has been used as a key starting material for the synthesis of a new drug for the prevention of breast cancer. The commercial demands for these compounds have created a need for their practical large scale production.

Diazonium salt reactions are generally employed to substitute a phenyl ring with a hydroxyl group. An isomerically pure hydroxythiophenol could thus be prepared by reacting an isomerically pure aminothiophenol with $NaNO_2$ and $H_2SO_4$ to form the corresponding diazonium salt, which could then be converted to a hydroxythiophenol by reaction with water.

The diazonium salt reaction with aminothiophenol, however, produces a poor yield of diazonium salt. Furthermore, aminothiophenols are sulfur-containing nucleophiles that tend to react violently with diazonium reagents. General methods for the preparation of thiophenols using the aryl Grignard-sulfur reaction are known in the literature, but, consistent with other hydroxy halide compounds, low yields are obtained. There remains a need for a commercially practical method of producing hydroxythiophenols in high yield.

DETAILED DESCRIPTION OF THE PREFERRED EMBODIMENT

This need is met by the present invention. It has now been discovered that the Grignard-sulfur reaction produces poor yields of hydroxythiol compounds because the well-known hydroxyl protecting groups typically employed with Grignard reactions form species upon de-protection that attack thiol groups. This is particularly a problem in the preparation on hydroxythiophenols. Therefore, significant quantities of isomerically pure hydroxythiol compounds may be produced by means of the Grignard-sulfur reaction if the species formed upon de-protection of the hydroxyl group is removed from the reaction mixture before it reacts with the newly-formed thiol group, or if a hydroxyl protecting group is employed that upon de-protection forms species that are inert toward thiol groups.

The present invention incorporates the discovery that previous attempts to synthesize hydroxythiol compounds using an Grignard-sulfur reaction were unsuccessful because of the protecting groups employed. For example, the commonly-used tetrahydropyranyl protecting group, formed dihydropyran upon de-protection, which attacked the newly-formed thiol group. By either using a hydroxyl protecting group that upon de-protection forms a species that is inert toward the thiol group, or that is removed from the reaction mixture before it reacts with the newly-formed thiol group, isomerically pure hydroxythiol compounds are produced in commercially useful yields.

The present invention thus provides an improved method for the preparation of hydroxythiol compounds in which, as shown in Step I, a hydroxyl-protected halogenated compound is reacted with magnesium in a Grignard-suitable solvent to form a hydroxyl-protected magnesium halide compound:

Step I

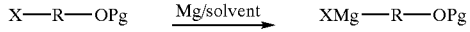

The magnesium halide is then reacted with sulfur in the Grignard-suitable solvent, as shown in Step II, to form a hydroxyl-protected, thiomagnesium halide, which may contain some di- and polysulfide species:

Step II

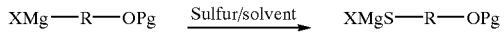

According to one embodiment of the method of the present invention, the hydroxyl protecting group is selected so that upon de-protection the species that are formed by the protecting group are inert toward thiols. In this aspect of the method of the present invention, the hydroxyl group may be hydrolyzed and de-protected, before the thiomagnesium halide is converted to the thiol.

According to another embodiment of the method of the present invention, when the hydroxyl group is de-protected, the species that is formed is removed from the reaction mixture before it reacts with the newly-formed thiol group.

In both embodiments, the reaction mixture is then treated with a reducing agent (to reduce the di- and polysulfide species that form). This increases the reaction yield. The de-protection, thiol conversion and reduction is shown in Step III:

Step III

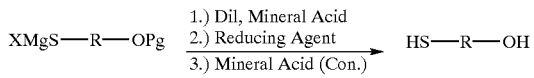

Because the reaction itself does not generate isomers, the method of the present invention is useful for the synthesis of isomerically pure regio-isomeric hydroxythiol compounds, and particularly useful for the synthesis of isomerically pure hydroxythiophenol compounds. Hydroxythiophenol synthesis is depicted in Steps I–III when R is an unsubstituted or substituted phenyl group.

For purposes of the present invention, an "isomerically pure" reaction product contains the same level of isomeric impurities as its starting material. Therefore, with the method of the present invention, the isomeric purity of the reaction product will depend upon the isomeric purity of its starting material, and it is possible to obtain an isomeric purity of 95 wt % and greater.

Thus, to obtain an isomerically pure end product, an isomerically pure starting material must be employed. Such materials are also commercially available or may be prepared by known methods. Isomerically pure halogenated phenols and alkylphenols, when not available commercially, are prepared using well-known halogenation reactions that are essentially conventional. Suitable reagents, solvents and process conditions may be determined by reference to March, J., *Advanced Organic Chemistry* (2$^{nd}$ Ed., McGraw-Hill, 1977), (the disclosure of which is incorporated herein by reference) and through routine optimization of reaction parameters. The alkyl and aryl halide isomers that form have distinct boiling points and are separated on a commercial scale by distillation.

Another aspect of the present invention, provides intermediate compounds having the structure of Formula I:

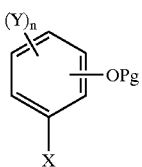
(I)

Y is selected from straight-chained or branched, unsubstituted or substituted $C_1$–$C_{20}$ alkyl, aryl, aralkyl, tertiary amino, amido and alkoxyl groups; n is between 0 and 4, inclusive; Pg is a protecting group that upon de-protection forms a species that is inert toward thiols; and X is selected from SH, Z, MgZ and SMgZ, wherein Z is selected from F, Cl, Br and I.

The method of the present invention utilizes halogenated hydroxyl compounds as starting materials. The compounds are commercially available. Alternately, they may be prepared using the conventional techniques described above. The hydroxyl group is protected with a suitable protecting group, to provide a compound having the structure of Formula II:

X—R—OPg (II)

wherein X and Pg are as described above for Formula I and R is a substituted or unsubstituted aliphatic radical, a substituted or unsubstituted cyclic aliphatic radical, a substituted or unsubstituted aromatic radical, a substituted or unsubstituted araliphatic radical or a substituted or unsubstituted heterocyclic radical.

More preferably, R is a substituted or unsubstituted, straight-chained or branched $C_1$–$C_{20}$ alkyl radical, a substituted or unsubstitued $C_3$–$C_{10}$ cycloalkyl radical, a substituted or unsubstituted $C_6$–$C_{15}$ aryl radical, a substituted or unsubstituted $C_7$–$C_{13}$ aralkyl radical, or a substituted or unsubstituted 3–6 member heterocyclic radical. Essentially any substitution group that is inert toward Grignard reagents or is capable of being protected from reaction with Grignard reagents may be employed. Suitable substitution groups, substitution groups requiring protecting groups, protecting groups and methods of protection are well-known. Pg may be used as a protecting group. Examples of substitution groups include $C_1$–$C_6$ aliphatics such as alkyls, alkoxys and alkenyls, $C_6$–$C_{15}$ aryls, $C_3$–$C_8$ cyclic aliphatics, tertiary aminos and amidos. The substitution groups may be straight-chained or branched and substituted or unsubstituted, as well.

R as a $C_1$–$C_{20}$ alkyl radical may be, for example, a methyl, ethyl, n-propyl, isopropyl, n-butyl, isobutyl, tert-butyl, n-pentyl, neopentyl, n-hexyl, n-heptyl, n-octyl, or 2-ethylhexyl radical. Any of these groups may be substituted with methoxy, ethoxy, n-propoxy, isopropoxy, n-butoxy or methanesulphonyl, to form, for example, methoxymethyl, 2-methoxyethyl, 2-ethoxymethy, n-butoxyethyl, 3-methoxypropyl, 1-methoxybutyl, 2-methoxybutyl, methanesulphonylmethyl or 2-methanesulphonylethyl. In a preferred class of alkyl radicals, R is a straight chain $C_2$–$C_6$ alkyl radical, especially a ethyl or butyl radical.

R as a $C_3$–$C_{10}$ cycloalkyl radical may be, for example, a cyclopropyl, cyclobutyl, cyclopentyl, methylcyclopentyl, cylcohexyl, methylcyclohexyl dimethylcyclohexyl, cycloheptyl, or cyclooctyl radical. Any of these groups may be substituted by methoxy, ethoxy, n-propoxy, isopropoxy or n-butoxy. In a preferred class of cycloalkyl radical, R is a $C_6$–$C_8$ cycloalkyl radical, even more preferably, a dimethylcyclohexyl radical.

R as a 3–6 ring member heterocyclic radical may include known heterocyclic atoms such as N, O and S. Suitable heterocycles include, for example, pyran, thiophene, pyrrole, furan, pyridine, or derivatives thereof R as a $C_6$–$C_{15}$ aryl may be, for example, phenyl, o-tolyl, m-tolyl, p-tolyl, o-xylyl, m-xylyl, p-xylyl, alpha-naphthyl or beta-naphthyl. Any of these groups may be substituted, for example, with $C_1$–$C_{14}$ alkyl, aryl, aralkyl, amino (primary, secondary or tertiary), amido, alkoxyl or hydroxyl. In a preferred class of compounds, R is $C_6$–$C_{12}$ aryl, especially phenyl or naphthyl.

R as a $C_7$–$C_{20}$ aralkyl radical may be, for example, benzyl, 4-methylbenzyl, o-methylbenzyl, p-methylbenzyl, diphenylmethyl, 2-phenylethyl, 2-phenylpropyl or 3-phenylpropyl, and preferably a $C_7$–$C_9$ aralkyl, especially benzyl. Any of these groups may also be substituted, for example, with $C_1$–$C_{14}$ aryl, aralkyl, tertiary amino, amido or alkoxyl groups.

In a still more preferred embodiment, R is a aryl or aralkyl radical, so that the compound of Formula II is a hydroxyl-protected aryl halide. The compound is formed by protecting the hydroxyl group of a halogenated phenol or alkylphenol by conventional methods.

Examples of suitable protecting groups for Pg include silyl groups such as trialkyl-silyls, including trimethylsilyl, triethylsilyl, t-butyldimethylsilyl, $C_1$–$C_{10}$, alkyl and substituted alkyl groups may also be employed, including methyl and substituted methyl groups, such as methoxymethyl, t-butyl, dihydropyranyl groups; ethyl and substituted ethyl groups such as 1-ethoxyethyl, 1-methyl-1-methoxyethyl, and $C_6$–$C_{20}$ aryl and substituted aryl groups, and $C_7$–$C_{20}$ aralkyl and substituted aralkyl groups, such as benzyl and substituted benzyl groups, such as p-methoxybenzyl, and p-phenylbenzyl groups. 2-(Trimethylsilyl)ethoxymethyl (SEM) may also be used, which is an alkylsilyl, as well as a substituted methyl, protecting group.

Hydroxyl protecting groups that upon de-protection form protecting group species that are inert toward thiophenols include alkylsilyl groups, such as the aforementioned silyl protecting groups, SEM, and groups that form unreactive alcohols upon de-protection, including alkyl, aryl, aralkyl, alkoxy, aryloxy and arylalkoxy groups. Protecting groups that upon de-protection form species that are reactive toward thiophenols include groups that form species that are reactive with sulfur-containing nucleophiles, such as tetrahydropyran and t-butyl protecting groups.

When the aryl or aralkyl group of R is a phenyl or alkylphenyl group the compound of Formula II is an intermediate compound of Formula I in which X is F, Cl, Br or I and Y and n are as described above for Formula I. When n is zero, the compound of Formula I corresponds to the compound of Formula II in which R is an unsubstituted phenyl group, and when n is one or two, the compound of Formula I corresponds to the compound of Formula II in which R is a substituted phenyl or alkylphenyl group. Accordingly, Y of Formula I represents the groups with which the aryl and aralkyl groups of Formula I may be substituted, i.e., for example, straight-chained or branched, substituted or unsubstituted $C_1$–$C_{20}$ alkyl, aryl, aralkyl, tertiary amino amido or alkoxyl.

The hydroxyl-protected halide compound is then allowed to undergo the Grignard reaction of Step I using magnesium in a conventional Grignard-suitable solvent. This reaction step is essentially conventional, and suitable reagents, solvents and process conditions may be determined by reference to the above cited March, J., Advanced Organic Chemistry (the disclosure of which is incorporated herein by reference) and by routine optimization of reaction parameters. Typically, an ether is employed as a Grignard solvent. Examples of suitable ethers include tetrahydrofuran (THF), diethyl ether, isopropyl ether and methyl tert-butyl ether (MTBE).

A magnesium halide compound is obtained having the structure of Formula II, in which R and Pg are as described above with respect to Formula II and X is selected from MgF, MgCl, MgBr and MgI. When R is a phenyl or alkylphenyl group, the compound of Formula II is an intermediate compound of Formula I in which X is MgF, MgCl, MgBr or MgI and Y and n are as described above for Formula I. When n is greater than zero, Y of Formula I again represents the groups with which the aryl and aralkyl R groups of Formula II may be substituted.

The magnesium halide compound is reacted as depicted in Step II with elemental sulfur suspended in a dry Grignard-suitable solvent under an inert atmosphere such as nitrogen.

This reaction step is also essentially conventional, and suitable reagents, solvents and process conditions may be determined by reference to the above-cited Advanced Organic Chemistry and by routine optimization of reaction parameters.

A thiomagnesium halide compound is thus obtained, having the structure of Formula II, in which R and Pg are as described above with respect to Formula II and X is selected from SMgF, SMgCl, SMgBr and SMgI. When R is a phenyl or alkylphenyl group, the compound of Formula II is an intermediate compounds of Formula I in which X is SMgF, SMgCl, SMgBr or SMgI and Y and n are as described above for Formula I. When n is greater than zero, Y again represents the groups with which the aryl and aralkyl R groups of Formula II may be substituted.

As depicted in Step III, the thiomagnesium halide compound is treated with a dilute aqueous mineral acid such as a 10% solution of an acid such as hydrochloric acid or sulfuric acid to effect hydrolysis and de-protection of the hydroxyl group. This reaction step is also essentially conventional, and suitable reagents, solvents and process conditions may be determined by reference to the above-cited Advanced Organic Chemistry and by routine optimization of reaction parameters.

The protected hydroxyl group may be hydrolyzed and de-protected either before or after the thiophenol group is formed. If the protected hydroxyl group is hydrolyzed first, then the resulting compound has the structure of Formula II, in which R is as described above with respect to Formula II, Pg is H and X is selected from SMgF, SMgCl, SMgBr and SMgI. If the thiophenol is formed first, then the resulting compound has the structure of Formula II in which R and Pg are as described above with respect to Formula II and X is SH. For either compound, when R is a phenyl or alkylphenyl group, the compound of Formula II is an intermediate compound of Formula I in which X is SH and Y and n are as described above for Formula I. Y again represents the groups with which the aryl and aralkyl R groups of Formula II may be substituted.

If the protecting group species that is formed by de-protection of the protecting group is not inert toward thiol groups, then the protecting group species should be removed from the reaction mixture before it reacts with the newly formed thiol group. The species that forms can be removed by essentially conventional techniques, including distillation, extraction with water or reaction with a stronger nucleophile than the thiol group. In fact, the hydroxyl group can be de-protected before the thiophenol group is formed when a nucleophile is added that is strong enough to react preferentially with the de-protected species over the newly-formed thiol group, thereby consuming the species that form upon de-protection.

Following the treatment with the dilute acid, Step III continues with the treatment of the organic layer with a reducing agent such as a mixture of sodium metabisulfite and KOH, a mixture of a metal (such as Zn, Fe or Sn) and $H^+$ or metal hydrides, such as $NaBH_4$ or $LiAlH_4$, at an elevated temperature up to the reflux temperature to reduce any di- and polysulfide species that have formed. Acidification of the aqueous layer with a concentrated mineral acid such as hydrochloric acid or sulfuric acid is performed if a basic reducing agent is employed. Th desired product is thus obtained, which is extracted into an organic solvent such as toluene, diethyl ether, isopropyl ether, methyl tertbutyl ether or halogenated solvents such as dichloromethane or chloroform. These steps are also essentially conventional, and suitable reagents, solvents and process conditions may be determined by reference to the above-cited Advanced Organic Chemistry or through routine optimization of reaction parameters. When R of Formula II is phenyl, the product is a hydroxythiophenol.

EXAMPLES

Example 1

Preparation of Isomerically Pure 3-Hydroxythiophenol

Isomerically pure 3-trimethylsiloxylbromobenzene was prepared by dissolving isomerically pure 3-bromophenol (486.8 g, 2.8 mol) in THF (2340 mL) containing pyridine (294.5 mL, 3.6 mol) in a 5 L three-necked round-bottomed flask equipped with a reflux condenser, an addition funnel and a mechanical stirrer. To this solution trimethylchlorosilane (464.8 mL, 3.6 mol) was added carefully by way of the addition funnel under nitrogen with stirring over about a 45-minute time period. White crystalline solids were formed rapidly, and the reaction temperature rose to 50° C. The reaction was stirred until completion as shown by GC (disappearance of the 3-bromophenol peak). The reaction mixture was allowed to cool to room temperature and the white crystalline solids were removed by vacuum filtration using a Buchner funnel. The white solids were washed with THF (2×200 mL). The filtrate was concentrated under reduced pressure to obtain the crude product as a liquid (containing a small amount of white solid). Vacuum distillation afforded 642 g of pure product as a colorless, clear liquid (94% yield).

Isomerically pure 3-trimethylsiloxylphenylmagnesium bromide was then prepared by heating a dry 5 L three-necked round-bottomed flask charged with magnesium turnings (55.1 g, 2.26 mol) to 110° C. under nitrogen using a heating mantle. The flask was then allowed to cool slowly to about 85° C. at which iodine (400 mg) was quickly introduced. THF (1224 mL) was introduced to the flask when the pot temperature dropped below 40° C. Stirring was started followed by the addition of 40 mL of the 3-trimethylsiloxylbromobenzene. The pot temperature was raised to 36° C. and the Grignard reaction initiated. The reaction temperature was kept at 46–50° C. during addition. The addition funnel was rinsed with THF (117 mL) and the contents were added to the reaction mixture. The progress of the reaction was followed by GC until the disappearance of the 3-trimethylsiloxylbromobenzene peak. The Grignard concentration was determined by titration following a literature procedure to be 0.9 M, which translated to 1.55 moles of Grignard reagent (76% yield). The Grignard solution was kept at 40° C. before use to avoid crystallization.

3-hydroxythiophenol was then prepared by charging a dry 12 L jacketed flask purged with nitrogen, with sulfur powder (52.1 g, 1.6 mol) and THF (585 mL). The mixture was cooled to 5° C. with stirring followed by addition of the above Grignard solution via a Teflon transfer line by applying $N_2$ pressure. The rate of the Grignard reaction was adjusted so that the reaction temperature could be kept below 15° C. The Grignard flask was rinsed with THF (2×234 mL) and the rinsed solution was added to the reaction mixture. The reaction mixture was allowed to warm to room temperature and stirred until a negative Gilman test was obtained. To the resultant mixture was then added 10% aqueous HCl (1158 g) in one portion. The pot temperature rose to 50° C. The reaction was stirred for one additional hour while cooling to room temperature. The bottom aqueous layer was drained off from the top THF layer and was treated with a solution of KOH (508 g) and $Na_2S_2O_5$ (212.7 g) in water (1740 mL). The resultant mixture was heated at reflux for two hours. The THF layer was separated and concentrated. The residue was combined with the aqueous layer, which was washed with butyl methyl ether (2×1170 mL). The aqueous phase was acidified to pH 1 with concentrated HCl. The resultant mixture was then extracted with t-butyl methyl ether three times (1560, 1170 and 780 mL) and the combined organic layer was washed with brine (780 mL). Removal of the solvent under reduced pressure while keeping the water bath temperature less than 30° C. afforded the crude product (181.6 g) as a slightly yellow liquid. Vacuum distillation using a Vigruex distilling column gave phenol (16 g), 3-hydroxythiophenol (135.7 g) and a high boiling point residue (29.9 g). The yield of the desired product was 53%, and purity was greater than 99%, as determined by GC.

Example 2

The method of Example 1 is performed using a dihydropyranyl protecting group. Treating the reaction mixture with 10% aqueous HCl following the Grignard reaction results in the re-formation of dihydropyran, which is removed from the reaction mixture by distillation. The organic layer is then treated with KOH and $Na_2S_2O_5$ to obtain the thiol group.

Example 3

2-Hydroxythiophenol is prepared according to the method of Example 1, using as the starting material 2-iodophenol.

Example 4

4-Hydroxythiophenol is prepared according to the method of Example 1, using as the starting material 4-chlorophenol.

Example 5

2-Thio-4-hydroxytoluene is prepared by the method of Example 1, using as the starting material 2-bromo-4-hydroxytoluene.

Example 6

2-Thio-3-hydroxy-p-xylene is prepared according to the method of Example 1, using as the starting material 2-chloro-3-hydroxy-p-xylene.

Example 7

4-Hydroxybutyl mercaptan is prepared according to the method of Example 1, using as the starting material 4-hydroxybutyl chloride.

Example 8

2-Mercaptoethanol is prepared according to the method of Example 1, using as the starting material 2-bromoethanol.

Example 9

Isomerically pure (−)-cysteine is prepared according to the method of example 1, using as the starting material isomerically pure (−)-3-chloro-2-aminopropionic acid. Before the Grignard reaction is performed, the amino and carboxylic acid groups are appropriately protected.

Example 10

2-Mercapto-6-hydroxylbenzothiazole is prepared according to the method of Example 1, using as the starting material 2-iodo-6-hydroxybenzothiazole.

The present invention thus provides a practical, commercially viable method for preparing isomerically pure hydroxythiophenols from readily available starting materials.

What is claimed is:

1. A compound having the structure:

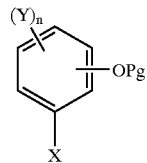

wherein Y is selected from the group consisting of $C_1$–$C_{20}$ straight-chained and branched aliphatic groups, $C_6$–$C_{15}$ aryl groups, $C_3$–$C_8$ cyclic aliphatic groups, tertiary amino groups and amido groups; Pg is a protecting group that upon de-protection forms a species that is inert toward thiophenols; n is between 0 and 4, inclusive, and X is SMgZ, wherein Z is selected from the group consisting of F, Cl, Br and I.

2. The intermediate compound of claim 1, wherein X is meta to OPg.

3. The intermediate compound of claim 2, wherein Pg is selected from the group consisting of alkylsilyl, alkyl, alkoxy, aryl, aryloxy, aralkyl and arylalkyoxy protecting groups.

* * * * *